(12) United States Patent
Liu

(10) Patent No.: US 6,368,279 B1
(45) Date of Patent: Apr. 9, 2002

(54) TIME-DELAY COMPENSATION SYSTEM AND METHOD FOR ADAPTIVE ULTRASOUND IMAGING

(75) Inventor: D-L Donald Liu, Issaquah, WA (US)

(73) Assignee: Siemens Medical Solutions, USA Inc., Iselin, NJ (US)

( * ) Notice: Subject to any disclaimer, the term of this patent is extended or adjusted under 35 U.S.C. 154(b) by 0 days.

(21) Appl. No.: 09/663,079

(22) Filed: Sep. 15, 2000

(51) Int. Cl.[7] .............................................. A61B 8/00
(52) U.S. Cl. ..................................................... 600/443
(58) Field of Search ................................. 600/443, 447, 600/444, 448, 437; 128/916

(56) References Cited

U.S. PATENT DOCUMENTS 5,697,372 A * 12/1997 Hughes ...................... 600/437
6,071,240 A * 6/2000 Hall et al. ................... 600/443

\* cited by examiner

Primary Examiner—Marvin M. Lateef
Assistant Examiner—Maulin Patel

(57) ABSTRACT

An ultrasound imaging system directs a transmit beam of ultrasound from a plurality of elements in a transducer array into a region of interest (ROI) of a patient's body. The receive beam back from the ROI contains a separate waveform for each of the array elements. These waveforms are partitioned into groups, and a control waveform is determined for each group. The control waveform is then jittered, that is, time-shifted, by a trial delay time, and trial delay times for the other waveforms in the group are determined by interpolation. A waveform similarity factor (WSF), which is preferably a function of the r.m.s. value of the sum of the waveforms in the group, is then evaluated. The control waveform is then repeatedly shifted by different trial amounts, with a new WSF being determined for each trial shift. The trial delay for the control waveform is then assumed to be optimum that yielded the greatest group WSF. A global time compensation profile for the entire array is then determined by interpolation, given the locally optimal time delays of the various control waveforms. This global profile is then applied by a beamformer to compensate the receive beamforming and subsequent transmit beamforming to generate the ultrasound image. The array may also be two-dimensional. The user may select, using input devices and visual feedback, a portion of the displayed ultrasound image to identify a region of interest. The optimum time compensation is then calculated based on the waveforms only in this region, but is applied by the beamformer to the entire displayed image.

15 Claims, 4 Drawing Sheets

TIME-DELAY COMPENSATION SYSTEM AND METHOD FOR ADAPTIVE ULTRASOUND IMAGING

BACKGROUND OF THE INVENTION

1. Field of the Invention

This invention involves a system and a related method of operation for an ultrasound imaging system, in particular, for compensating for the effects of different time delays of the elements in an ultrasound transducer array.

2. Description of the Related Art

A modern ultrasound imaging system works by transmitting into a region of interest (ROI or "interrogation region") of a patient's body a beam of ultrasound, which is formed as the composite of ultrasonic transmit signals from an array (one-or two-dimensional) of piezoelectric elements. By varying the relative phases and amplitudes of the transmit signals, the beam can be focused onto different points within the region of interest. The back-scattered signals then cause the array elements to vibrate and to generate electrical signals corresponding to the mechanical vibrations. This is of course well known.

Human tissue is not homogeneous. Indeed, if it were, then ultrasound imaging would be all but ineffective, because there must be some variation in acoustic impedance for ultrasound to be reflected back to the transducer array. One problem that arises because of this inhomogeneity, however, is that it causes differences in propagation times in the region between the array and the point of focus. These differences are unrelated to the structure of interest and reduce the ability of the system to properly align the return signals in time and thus the quality of the image created from the return signals.

A conventional ultrasound system focuses the transmit and receive beams by assuming the medium to be uniform with a known sound speed (typically 1540 m/s) and timing the firing of the different elements and time-gating the return signals in such a way that the assumed round-trip time to and from any given focal point is the same. In reality, since the tissue is not uniform, the propagation time from each element to the focal point deviates from the values calculated based on the assumption of a uniform speed of sound in the medium.

In order to compensate for propagation time errors, several different techniques have been proposed for creating time delay profiles for adaptively focusing the beams. According to one known method, the system determines the peak position of a time-domain cross-correlation of neighboring waveforms; the peak then gives the relative time delay to be applied. The system then constructs a delay profile by adding up all the individual relative time delays. In other words, this prior art system selects a first element then cross-correlates to get an estimate of the time delay to the adjacent, second element, then applies this delay to adjust the second waveform, then cross-correlates the second waveform with the third to get a correction for it, and so on, until a relative time delay is computed through cross-correlation for all the elements. One drawback of this method is that errors accumulate: Any error in the calculated time-delay for the second element (relative to the first) is also included in the cross-correlation of the second and third waveforms, and the increased error in this calculation propagates to the next cross-correlation calculation, and so on.

Yet another method involves cross-correlation of each return waveform with the beam-sum waveform. According to still another known technique, the system determines a reference waveform by adding several neighboring waveforms that have already been aligned using some other method. The time delay for each new waveform is then calculated by determining the peak of the cross-correlation between the new and reference waveforms. Yet another proposal involves forming redundant pairs of cross-correlations and then solving the resulting set of over-constrained equations using a least-mean-squared error method to synthesize a complete delay profile.

According to yet another proposed method, the delay for each waveform is adjusted in turn to maximize the image brightness. In this technique, the delay is adjusted randomly for one element at a time and the adjustment that resulted in maximum image brightness is retained.

One drawback of all these techniques is that they operate on only one waveform at a time, so that information contained in other, neighboring waveforms is ignored. Moreover, because of inhomogeneities, even adjacent waveforms often differ so much in shape (amplitude profile) that the auto-correlation technique may produce erroneous and unstable results. In the presence of a moderate amount of aberration, waveforms received by individual elements may sometimes be severely distorted with amplitude fluctuations, similar to the scintillation associated with the propagation of radio waves in the atmosphere. Similarly, maximizing the beamsum energy based on adjusting delays for individual elements may result in a spiky delay profile. The delay values determined using these techniques are therefore prone to error, and applying these values to correct beamforming may actually worsen the ultimately displayed image.

Newer techniques involving translating the transmit aperture of the transducer or creating common mid-point signals have also been proposed to acquire data for time-delay estimation. Each of these techniques, however, require multiple transmits and are therefore sensitive to motion artifacts. Moreover, as long as individual elements are used to derive the delay profile, the amplitude variability of individual waveforms will still cause problems in the delay estimation. Furthermore, those that depend on comparison with some reference waveform are also sensitive to the choice of the reference: If the reference is severely distorted, for example by significant and highly localized non-linearities, then all calculations based on it will be affected.

What is needed is therefore a way to estimate a time-delay profile that takes into account the variability of the shape (amplitude profile) of individual waveforms. Such a method should avoid the problems associated with a poor choice of some reference, and the problem of error accumulation inherent in those systems that compare neighbors pair-wise without some common reference. The estimated delay profile should align the waveforms as coherently as possible, that is, with maximum beamsum energy, and should also be smooth, that is, the profile should not display abrupt and therefore physically unlikely jumps. This invention provides a system and a related operating method that provides such a time-delay profile.

SUMMARY OF THE INVENTION

The invention provides an ultrasound imaging system and method of operation in which a transducer is activated to transmit into a region of interest of a patient's body a transmit beam of ultrasound from a plurality of elements in the transducer array. An echo signal is then received back from the region of interest, such that each transducer array element generates a respective receive waveform, the waveforms together constituting a receive beam.

An adaptive delay component or module within the processing system then groups the array elements into a predetermined number of groups and, for each group, it selects a control waveform corresponding to a designated control element of the array. For a first one of the groups, the processing system then selects an initial compensation time for the waveforms in the first group; it time-shifts the control waveform by a local time shift amount; it determines a local time compensation profile by interpolation between the local time shift amount and the initial compensation time; and it then calculates a local waveform similarity factor WSF (preferably a function of the r.m.s. value), of the sum of the waveforms in the group time-shifted according to the local time compensation profile. The processing system then time-shifts or "jitters" the control waveform again, interpolates to get time delays for the other waveforms in the group, and evaluates the corresponding WSF of the beam sum. This procedure is repeated, preferably using at first coarse and then fine trial delay steps for the control waveform, at which point the system will have calculated a plurality of WSF values. It then sets as a locally optimal time compensation value for the first group the local time shift amount for which the corresponding WSF value is a maximum.

This same procedure of time-jittering a control waveform in each group by a plurality of trial delay amounts, interpolating time delays for the remaining waveforms in the group, evaluating the WSF of the beam sum, and determining a locally optimal time delay for the control point is repeated for each group. The initial delay value assumed for each group is preferably the locally optimal value determined for the previous, adjacent group.

Once the system has determined locally optimal time compensation values for all the groups, it then calculates a global time compensation profile by interpolating from the initial time compensation value of the first group and over the locally optimal time compensation values for all the groups. Each receive waveform is then delayed, that is, time-shifted, by a beamformer according to the global time compensation profile, thereby forming a time-compensated receive beam. An image of the region of interest is then generated and displayed on a display as a predetermined function of the time-compensated receive beam.

In a two-dimensional embodiment of the invention, the array is a two-dimensional array. Each group of elements, and corresponding waveforms, thereby corresponds to a two-dimensional portion of the array.

The invention also provides a system for adaptive time-compensation for an ultrasound image in which the user uses input devices to select and designate a portion of the displayed ultrasound image as a compensation region. The system then optimizes the time delay compensation based on the waveforms in the selected compensation region. In other words, the system then preferably includes the time delay compensation arrangement summarized above and calculates an optimum time compensation profile as a predetermined function of those portions of those receive beams that correspond to the displayed compensation region. The time compensation profile determined for the selected compensation region is then applied to at least the displayed compensation region, and preferably to the entire displayed image. The transmit circuitry of the system is thereby preferably provided for focusing the transmit beams onto a user-selected time compensation base point; the compensation region is then preferably a portion of the displayed image that includes the time compensation base point.

DETAILED DESCRIPTION

First, the general method of the invention is described with reference to FIGS. 1 and 2. After that, an embodiment of the invention for operation with a one-dimensional array is described. Thereafter, an extension of the invention to provide time compensation for a two-dimensional array is described. Then, the main system components of the preferred embodiment of the invention are illustrated and discussed. Finally, a user interface according to the invention is described that is particularly advantageous for adaptive imaging at a user-specified location.

Adaptive Optimization of Time Compensation Profiles

Figure 1:
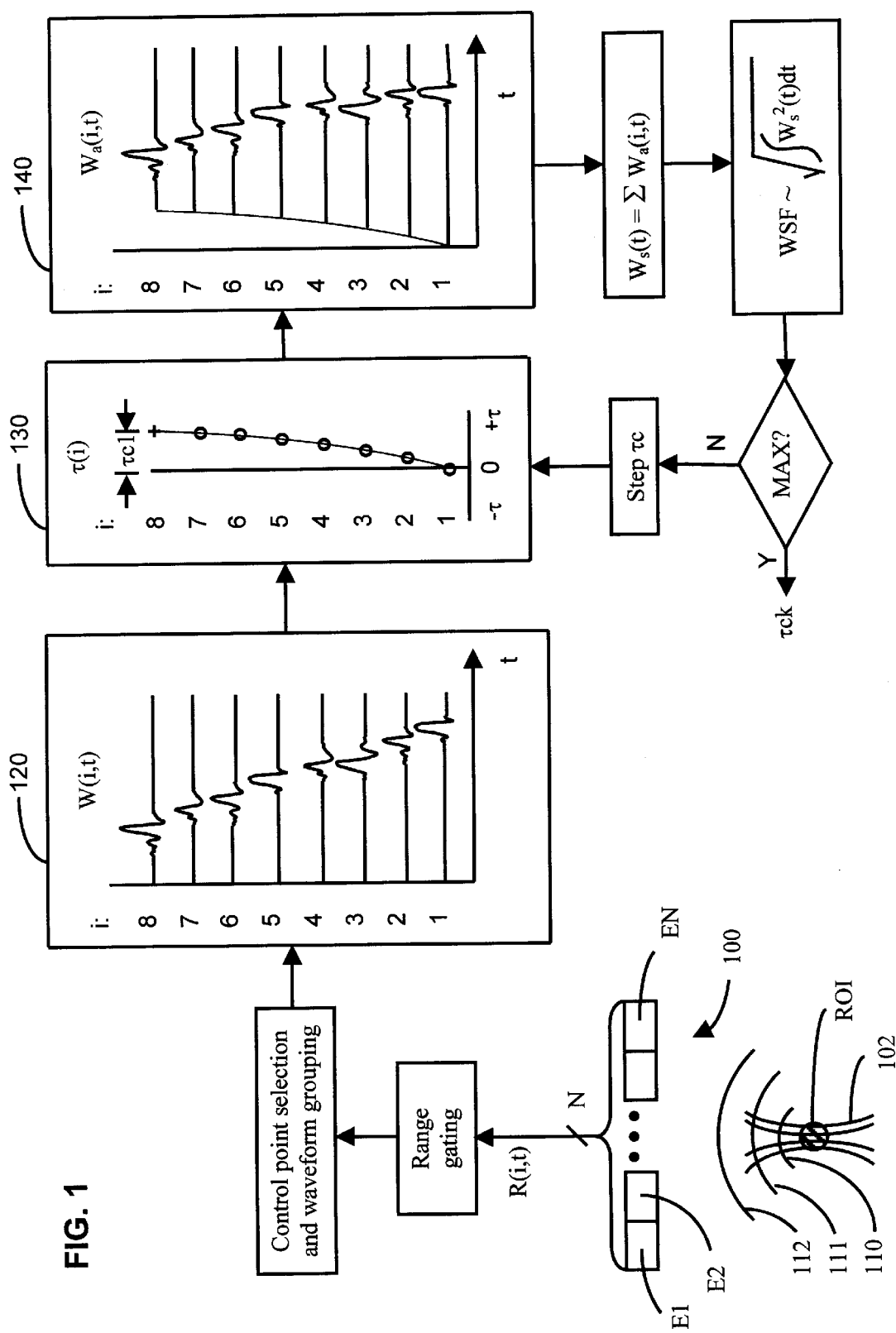
FIG. 1 illustrates the general principle and major processing steps performed according to the invention.
Figure 2:
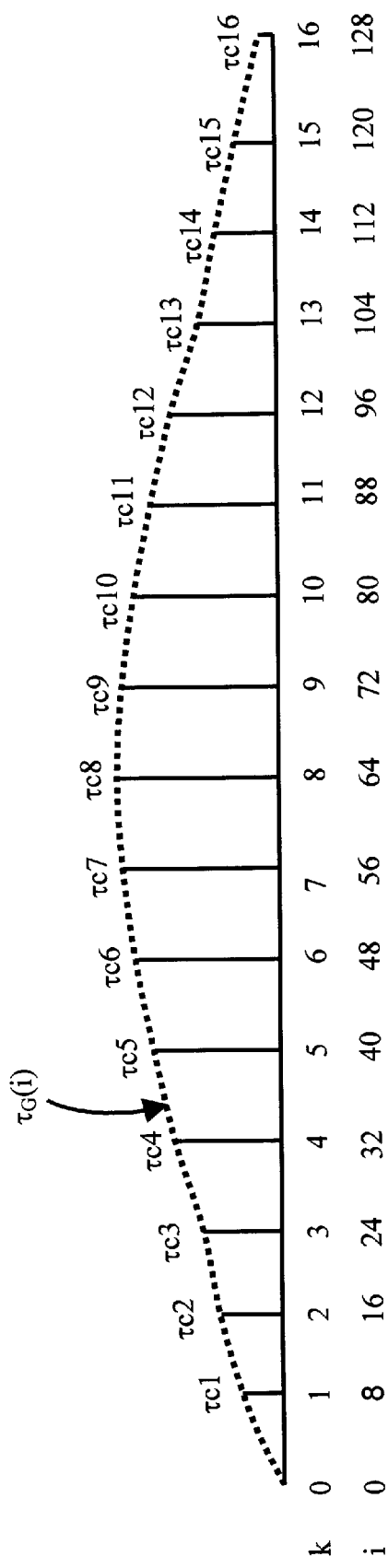
FIG. 2 illustrates an optimized time compensation profile that is determined using the invention for a linear ultrasound array.

FIG. 1 illustrates the general principle of the invention. Piezoelectric elements E1, E2, . . . , EN implemented as an array 100 within an ultrasound transducer are activated, using conventional circuitry (see below) to generate a pulse or beam of ultrasound that is comprised of the individual transmit signals 102 emitted by the respective elements. The number of elements in the array 100 may vary depending on the transducer frequency and format of scanning (for example, linear or phased). The invention does not require any particular number of elements; indeed, as is described below, the array need not even be linear, but rather could be a two-dimensional array of M*N elements.

Using known methods and circuitry, the beam is focused on a region of interest ROI within a patient's body by choosing the phases and amplitudes of the transmit signals. Ultrasound is then reflected back towards the array by any structure within the ROI with a sufficiently different acoustic impedance relative to its surroundings to create an echo. These back-scattered signals (wavefronts) are illustrated in FIG. 1 by the arcs 110, 111, and 112.

Notice that if the ROI were a single point, and the entire region between the array and the point were acoustically homogeneous, then each back-scattered wavefront would be a sphere, so that any two-dimensional projection would appear as a circular arc. In actual cases, of course, these assumptions are not met, and the returning wavefront has irregularities. Once the backscattered energy reaches the array elements E1, E2, . . . , EN, it causes them to vibrate mechanically and generate corresponding electrical signals $R(1,t), R(2,t), \ldots, R(N,t)$. The transmit and receive cycle is then repeated at a given pulse repetition frequency. This is of course well known and is found in every ultrasound imaging device.

Conventional beamform processing such as amplification, time-gating (to isolate the portion of the return signals corresponding to the depth of the ROI) is then applied to the return signals to generate corresponding waveforms $W(1,t), W(2,t), \ldots, W(N,t)$ on respective channels. The time-gating will be based on geometry of the transducer, the assumed depth of ROI, and the assumed uniform sound speed. Eight (one group—see below) of these waveforms, W(1,t), W(2,t), ..., W(8,t), are represented graphically in FIG. 1 within box 120. In FIG. 1, the waveforms are shown as continuous functions of time with an essentially zero amplitude except for a singe region where there is a "pulse." This has been done merely for the sake of clarity: In actual implementations of the invention, the return signals are converted into digital form using conventional analog-to-digital (A/D) conversion circuitry (see below), so that the waveforms W(i,t) are actually sequences of digital numbers. Furthermore, the waveforms will typically be much less smooth than those shown in FIG. 1, with non-zero amplitude over almost the entire waveform and a much less pronounced "pulse" region. The waveforms W(1,t), W(2,t), ..., W(N,t) will usually not aligned in time because of inhomogeneity of sound speed in the medium.

In FIG. 1, a time-compensation profile $\tau(i)$ is illustrated in box 130. As its name implies, the time-compensation profile determines by how much time each waveform i should be shifted in order to best align it with the others. The set time shift $\tau(8)$ for W(8,t), which, as is explained below, is a jittered control point, is shown by a "+" symbol; the other time shifts or adjustments, which are obtained by interpolating the control points, are shown by the symbol "o".

Assume that the time compensation profile in box 130 is applied to the eight waveforms W(1,t), ..., W(8,t), in effect shifting each waveform in the +t direction. In other words, for each waveform W(i,t), the system forms W(i,t-$\tau$(i)). The resulting time-aligned waveforms $W_a(1,t), \ldots, W_a(8,t)$ are illustrated in box 140.

The problem then becomes how to determine the best time alignment for the different waveforms. Of course, this raises the question of just what is meant by "best" alignment, and just how to quantify it for each waveform. As is mentioned above, prior art systems tend to rely on cross-correlation between pairs of waveforms in order to determine a time correction between neighboring pairs of waveforms. FIG. 1 also illustrates perhaps the main cause of errors in these known techniques: The waveforms W(i,t) are not usually identical in shape even if they are aligned in time, and the more dissimilar they are, the more error-prone cross-correlation becomes.

The invention overcomes this weakness as follows:

Assume simply by way of example that there are 128 evenly spaced elements E1, E2, ..., EN (N=128) and denote the corresponding received waveforms sequentially as W(1,t), W(2,t), ..., W(128,t), which have already been shifted using conventional techniques based on geometric time-delay calculations. The system according to the invention then selects a predetermined number of the elements as "control" or "base" points, which, for the sake of ease of indexing and computation, are preferably evenly spaced across the wavefront in the space (channel) direction. Their corresponding waveforms are then designated as control waveforms. For example, 16 control points P1, P2, ..., P16 could be selected, so that the collection of receive waveforms is divided into 16 groups of eight each. Thus, if elements 8, 16, 24, ..., 128 are selected as control points, then the waveforms W(8,t), W(16,t), W(24,t), ..., W(128,t) would be control waveforms corresponding to the control points P1, P2, ..., P16. The waveforms W(1,t), ..., W(8,t) would be in the first group, and so on, up to waveforms W(120,t), ..., W(128,t), which would be in the 16$^{th}$ or last group. This number and grouping of elements is assumed below and illustrated in FIG. 1 merely by way of example: The selection of control points will depend upon the element pitch as well as the aberration characteristic of the medium; the choice of control points corresponds to a spatial sampling of the delay profile that will be eventually formed and is therefore governed by Shannon's sampling theorem. It will be obvious to those skilled in the art to extend the method described below to arrays with a different number of elements, with a different number or distribution of control points, with different groupings, or with any or all of these modifications.

Of course, other distributions of control points can be chosen. For example, one could select a "middle" element (and corresponding waveform) in each group as the control. Simply choosing the control points to be the separators between adjacent groups (that is, one end point in each of two adjacent groups), however, has proven to be easy to implement in software and to provide good results.

Furthermore, the spacing of control points does not have to be even, especially not if it is found that waveforms from elements, for example, near the ends of the array, are more prone to irregularities. In this case it may be beneficial to group them with more other elements to better correct for their irregularities, or fewer elements to reduce their effect on others. Once again, though, even spacing has been shown to provide good results while also being the easiest to implement. The choice of grouping, including the number of elements and waveforms in each group, can be made using normal experimental and design methods.

One advantage of the invention, however, is that waveforms need not be compared only in pairs (a limitation of cross correlation-based methods) but rather that information in three or more waveforms can be used at a time to determine the optimum time delay compensation; this thus takes better into account the known property that time distortions are typically highly correlated for elements extending over groups of more than two, especially for transducers arrays with fine pitch between adjacent elements. One could, in the limit, consider each element/waveform to be a "group," and evaluate a pair of waveforms by jittering or time-shifting one waveform relative to the other in order to find a maximum r.m.s. value of their sum, although this will typically be slower and more error-prone than grouping at least three waveforms at a time into each group.

The general method of the invention is as follows: Assume that waveforms W(1,t), W(2,t), ... W(N,t) are separated into K groups and assume that the first group to be optimized is the k'th group (for example, the group at the center of the array). This group, like other groups, has two control points, say, P and Q. The system arbitrarily selects one of the control points, for example, P, to serve as a reference point for the entire array, so it's delay will be fixed at zero. The other control point Q is then assigned different trial delay values. For each value, all the control points existing from Q to the end of array are preferably also assigned the same value, as if all the rest of the control points are moving together with control point Q. For each trial value, the degree of alignment is evaluated for waveforms between control points P and Q. This is done by first interpolating the control points to generate delay values for the waveforms between control points P and Q, time-shifting those waveforms using the generated delay values, and then computing the waveform similarity factor (WSF) as described below.

After the optimal delay value for point Q is determined, for example using the coarse/fine search described below, to maximize the WSF for the waveforms between points P and Q, the system proceeds to the next control point, which may be symbolically denoted as Q+1 (the next point toward the array end, away from point P). The procedure of testing the delay values and maximizing WSF for the waveforms between control points P and Q+1 is then repeated.

The system then proceeds to Q+2. In this case, the evaluation of alignment may be between P and Q+2, or, to save computation, between Q and Q+2, omitting the portion between P and Q. The number of groups evaluated at any given step is preferably limited to two, which reduces the computational burden while still making use of the degree of correlation normally found between waveforms in adjacent groups. Of the two groups, one group is already aligned and can serve as the "anchor point" for the next group. Assuming that the control point P is not the beginning of array, that is, that the first group was not an end group of the array, the system must then also evaluate the waveforms in groups located at the other end of the array. The system thus adjusts the time delay values for control points P-1, P-2, etc. (Recall that it is assumed that the delay of the control point P is a reference, with a delay defined to be zero.) Control points are thus adjusted one at a time and based on maximizing the WSF of the portion of waveforms that it affects. These procedures, and various alternatives, will now be described more specifically.

Refer once again to FIG. 1. According to the preferred embodiment of the invention, once the waveforms are divided into groups (that is, once the control points are assigned), an optimum time adjustment is determined for each control point in turn, starting with a first group. This first group may be, for example, one of the end-most groups, the center-most group, the group with the greatest beamsum energy, etc., depending on the chosen implementation—the order of processing of the groups can be chosen using normal design methods.

When time-aligning the first group of waveforms, such as the illustrated W(1,t), ..., W(8,t), an initial time compensation of zero is preferably assumed for all the elements in the group, unless there is some theoretically or experimentally determined reason to assume some other initial delay profile. A first, jittered time compensation $\tau c1$ is then assigned for the control waveform for group k (here, k=1). In other words, given the values and groupings used in this example, W(8,t) (corresponding to the assumed control element in the first group of eight elements) is time-shifted to become W(8,t-$\tau c1$). This represents a first time "jittering" or "shift" for this control point. A first local group time compensation profile (function) $\tau(i)$ is then calculated as an interpolation between the trial time delay of the control point and the initial time delay, that is, from the time delay (initially assumed to be zero) of the waveform (here: W(1,t)) farthest from the control point to the time delay $\tau(8)=\tau c1$ of the control waveform (here: W(8,t)) of the group.

Each waveform in the group is thus time-adjusted to form $W_a(i,t-\tau(i))$. Expressed in words, a time adjustment (shift) is postulated for the current control point, and then each other waveform in the respective group is time-shifted by an amount determined by interpolation from the control point's time delay to the current time delay (initially assumed to be zero) for the waveform at the other "end" of the group from the control point.

In FIG. 1, the result of applying the interpolated time compensation profile $\tau(i)$ is shown in box 140. Note that the waveforms are better aligned in time, but that the alignment is still far from ideal, even given the different shapes of the pulses in each waveform: They are better aligned than when they were first received (box 120), but especially the higher-indexed waveforms are not lagged enough to align with the others. Again, however, the system according to the invention must quantify this mis-alignment. The preferred method will now be explained.

At this point, the control waveform in the group will have been time-shifted by a predetermined amount (explained above) and each other waveform in the group will have been time-shifted by an interpolated amount. The system according to the invention then sums all the time-shifted waveforms in the group to form a beam-summed waveform s(t), and thereafter calculates a waveform similarity factor (WSF) for s(t), where WSF quantifies a degree of alignment for a given group of waveforms. In the preferred embodiment of the invention, WSF is computed as a predetermined function of the r.m.s. value of the beam sum of all the time-shifted waveforms in the group.

$s(t)=\text{SUM}\{W_a(i,t-\tau i); i=1 \text{ to } N\}$
$L[f(t)]=\text{SQRT}\{\text{INT } f(t)^2 \, dt\}$
$\text{WSF}=L[s(t)]/\{L[W(1,t-\tau 1)]+L[W(2,t-\tau 2)]+ \ldots +L[W(N,t-\tau N)]\}$ where
s(t) is the beam sum of the N adjusted waveforms in the current group;
$\tau i$ is the interpolated time compensation for waveform i;
L[f(t)] indicates the root mean square of any given function f(t);
WSF is the waveform similarity factor computed for the group;
INT indicates integration over the entire time interval of the waveforms;
and
SQRT indicates the square root function.

Generally, given the delay values at the K control points P1, P2, ..., PK a delay profile for all N received waveforms can be generated by interpolation. However, it will usually be necessary to generate the delay values only for the waveforms that are going to be affected, which are in the vicinity of (for example, within one or two groups of) the control point that is currently being jittered.

There are several advantages of using the r.m.s. value of the beam-summed waveform s(t) as the measure of alignment of the component waveforms. One advantage is that it allows for easy normalization, using known algorithms, to within a set interval such as [0,1], and thus provides a uniform measure of the "goodness" of a particular jittering of a control point. Another advantage is that a normalized measure allows a meaningful comparison of the alignment of different groups.

Still another advantage is that the r.m.s. value is related to a physical quantity, namely, power, of a given beam sum; this in turn gives an indication of the relative signal strength received by the different element groups. This information is often used in other aspects of ultrasound imaging. In the context of the preferred embodiment of the invention (described below), however, the final time compensation profile for all elements in the array is determined by a single interpolation based on the individually, locally optimized delay values of the various control points. Assume that one or more groups have an r.m.s. value (preferably normalized) lower than some predetermined threshold, or less than a predetermined percentage of the maximum or average r.m.s. values of the other control points. The system according to the invention could then be set to eliminate such low-valued control points from the interpolation.

It is of course possible to use other measures of similarity besides the r.m.s. value, normalized or not, of the summed waveforms. For example, since the locally optimized time shift for an given control point is a function of the maximum of the WSF, the simple integral (sum) of $s(t)^2$ will yield the same optimum as the r.m.s. measure. Similarly, one need not normalize at all. Those skilled in the art will be able to design and implement still other measures for WSF depending on how they choose to define "similarity" of waveforms for the purpose of time alignment. For example, one could choose to maximize the amplitude of one or more spectral components of s(t).

The control point is then time-shifted or "jittered" again, for example, to 2*τc1; a new time-compensation profile is calculated by interpolation for the other waveforms in the group; a new beam sum s(t) is calculated; and a new WSF based on the new s(t) is calculated. This process is carried out additional times, so that several WSF values are obtained for the first group, each value corresponding to the group waveforms shifted according to the time compensation profile interpolated from one "jittering" (time shift) of the control waveform.

After the jittering process is completed, one of the interpolated time compensation profiles—$W_{max}(i,t)$— corresponding to a respective jittered value of τck for the group's control point, will have yielded the maximum WSF value for the waveform group. This interpolated time compensation profile $W_{max}(i,t)$ can then be taken as the final compensation profile for the group. In the preferred embodiment of the invention, however, the final time delay or compensation profile for all elements is determined as a spline (or other) interpolation between the optimum time delay values τck for all the control points taken as a whole. In other words, the local interpolations are used to optimize the time delay of the respective control waveform, but the final time compensation profile is calculated as a global interpolation over all the locally optimized control point time shifts τck.

Observe that it is not certain that the time by which the control point should be jittered will lie in the +τ direction, shown as in box 130 of FIG. 130. Indeed, this will normally vary from group to group. Accordingly, the control waveform is preferably jittered in both the +τ and −τ directions (as well as, initially not jittered at all) predetermined number of times.

The amount by which the control waveform is initially jittered, that is, the step size by which the control waveform is initially and then subsequently time-shifted, may be either predetermined and fixed, or adaptive. In one prototype of the invention, each control waveform was first evaluated as is (unjittered) and then jittered in both the +τ and −τ directions with a step size of 2T, where T was the sampling interval of the system. For a 50 MHz sampling rate of the received signals R(i,t), the step size was thus 40 ns. Obviously, the smaller the step size the system uses, the longer it will normally take to find the best time compensation profile for the elements in each group. On the other hand, too large a step size will usually result in selecting a less than optimum time compensation. Normal design methods may be used to determine a suitable step size for any given implementation of the invention.

When using fixed step sizes, it is also necessary for the system to have a cutoff point, that is a limit to the number τ(i) adjustment steps for each group after which it accepts the compensation profile which yielded the highest WSF value. In the prototype of the invention described above, with a 40 ns step size, it was found adequate to perform five coarse adjustment steps (τci=0, and two steps in both the positive and negative τ directions) for the control point of each group. The only theoretical limit of the amount of jittering would be the size of the range gate used to acquire the waveforms—steps cannot be larger than the waveform itself. In practice, however, no such large step size is required, since such extreme misalignment would occur only for waveforms so distorted by noise that time-gain compensation would be all but useless anyway.

A coarse-fine jittering strategy is used in the preferred embodiment of the invention. According to this method, a large jittering step size is used to find a coarse maximum for WSF. Thereafter, the corresponding adjusted control waveform is jittered in a predetermined number of smaller jittering steps about the coarse maximum, with a total amount of jittering being less than the size of a coarse jittering step. The greatest WSF found using these "fine" steps then indicates the optimum amount of jittering (that is, the best time delay) for that control point.

The size of the steps, both coarse and fine (if included), can be determined by known design methods and experiments. For example, one could simply set the coarse step size to a predetermined percentage of the range gate, with the fine step size being a percentage of the coarse step size. The step size(s) could also be made a function of transducer frequency, the ROI depth, the type of structure being imaged, etc.

Once the best time delay τc1 is determined for the first control point, the same optimization procedure is then carried out on the second group of waveforms. For this second group, however, the optimum time-compensation value previously calculated for the first control point is set as the initial time-compensation value for all waveforms in the second group. Interpolation is then done between this set optimum value for the first control point and the successive jittered time delays τc2 of the second control point.

It would be possible to determine τc2 (and subsequent optimum control point delays) based solely of the WSF values for the interpolated compensation profiles of the single corresponding group. In the preferred embodiment of the invention, however, once a control point (other than the first) is jittered, the WSF is evaluated for an adjusted time compensation profile that is interpolated over not only the current group, but also over at least one other earlier optimized group. This takes better into account the fact that waveforms from adjacent groups are often highly correlated, while still allowing a relatively fine partition of the elements into groups, and thus closer correspondence between the final, global time compensation profile and the locally optimized profiles $W_{max}(k,t)$.

Once the time-compensation profile is found that maximizes the WSF value for the second group, the system proceeds to iteratively determine the optimum profile for the third group of waveforms, and so on, until the final group has been locally optimized. At that point, a complete, optimum time compensation profile could be compiled simply as the concatenation of the locally optimized compensation profiles of the different groups.

As is mentioned above, however, a single final time compensation profile is preferably determined by a spline interpolation over the entire set of optimally adjusted control points at once. This is illustrated in FIG. 2, which shows the locally optimized time delays τck for each group k=1, . . . , 16 and a global interpolation curve $\tau_G(i)$, which indicates, for each element (waveform) i what time compensation the system should apply to it. Individual elements are of course spaced between the control points.

One advantage of determining a single final time compensation profile is that it requires storage of only a single set of parameters to define the profile. This makes for easier implementation in software and somewhat faster computation. Yet another, more important advantage, however, is that the single, final interpolation will be "smooth," that is, it will not have any abrupt change in time delay for adjacent elements. If interpolating splines are used, such that the interpolation passes through each of the locally optimized delay values, then this interpolation will also not introduce additional error deliberately into the time compensation for any control point.

Different types of interpolation may be used not only during local optimization, in which there may be only a few (for example, two, three or more, depending on how many previously optimized control points are included) control points at the boundaries of the interpolation range, and for global interpolation over all the in the locally optimized control points. Furthermore, different types of interpolation may be used for each.

The simplest form of local interpolation would be linear, between the time compensation values for the control points at either end of the element group. One problem of linear interpolation is that it takes into account the information in only two control points. Another problem is that actual true time compensation curves are almost always smooth, and not piecewise linear, so linear interpolation is certain to be introducing error with only a small gain in computation speed.

The preferred interpolation method is splines of any conventional order or type, such as quadratic, or higher-order polynomial, that pass through the locally optimized control points. Similarly, the coefficients of a single polynomial can be calculated using known algorithms and that passes through all the $\tau$ck points. Of course, other types of approximating functions may be used, such as trigonometric, least-squares best fit, etc., to provide interpolated time delay values for all the elements, given the $\tau$ck points, although these functions will typically cause more of a computational burden than splines with insignificantly better or possibly even worse accuracy, will not pass exactly through the locally optimized values, or both.

In the expressions above, the various waveforms are represented as continuous functions of time. This is merely to keep the explanation as simple and understandable as possible. Recall, however, that the waveforms are at this point stored in system memory in digital form, having resulted from the sampling, with a sampling period T, of the continuous receive waveforms generated by the elements. In the evaluation of WSF, these waveforms are delayed by values which are determined by interpolating the control points, and are usually not integer multiples of T. Therefore, the digitized waveforms are preferably interpolated by such methods as moving-average jittering or Lagrange interpolation to obtain delayed waveforms. The beam sum Ws can therefore be calculated quickly simply by performing sample-by-sample addition of the values of the waveforms included in the calculation.

Observe that WSF as defined above is a function of the m variables $\tau i$, where m is the number of waveforms used in the optimization and i identifies the respective corresponding waveform. Furthermore, WSF is defined for every sample point. The maximum of WSF can therefore be determined using other methods than the simple (and fast) fixed-step (or coarse-fine) search described above.

After taking at least one initial fixed step, the first derivative of WSF can also be estimated using known difference techniques. As such, known gradient-search and adaptive step algorithms such as Newton-Raphson can therefore also be used to calculate the maximum WSF. Such techniques that rely on the calculation of derivatives, however, are prone to become "stuck" in local extrema and are therefore less reliable in the context of received ultrasound waveforms than the fixed-step search techniques.

Moreover, other heuristic optimization algorithms (that is, those that do not rely on previous estimates of optima) can also be used. One of these is the well-known simplex routine, which does not require calculation of any derivatives of WSF. Indeed, it would in theory be possible to directly calculate the entire global compensation profile $\tau_G(i)$ at once, as the function that maximizes the N-variable "cost" function WSF. In practice, though, this may require too great a computational effort for an uncertain and probably unnecessary increase in accuracy.

Having calculated the global time compensation profile $\tau_G(i)$, using whichever method is chosen in a given implementation, the system according to the invention applies this profile to the received waveforms to time-align them. In other words, the waveform from each element is delayed in time by the amount of the corresponding value of the global time compensation profile. The time-aligned waveforms then make up a time-compensated receive beam, which is then applied as the beam-formed output to subsequent, conventional processing circuitry such as a scan converter, which converts the beam-formed signals into a form suitable for presentation on a conventional display.

The system will also utilize the obtained time compensation profile to improve the transmit beam. This has two consequences. First, the improved transmit beam will further improve image resolution. Second, the resulting smaller transmit focal spot size will cause echo signals to be more coherent (that is, similar to each other) and more suitable for use in time-delay estimation. The way in which a given time-compensation profile is applied to a transmit beam is known in the art and is therefore not discussed in greater detail here.

In the discussion above, it is assumed that the elements and waveforms are partitioned into a predetermined, fixed number of groups, and that a local optimum time compensation is calculated for each group individually. This is not necessary. Rather, an adaptive procedure could be used to reduce the computation time:

According to this adaptive procedure, an initial time compensation of, for example, zero, is assigned to all elements. A first group of elements/waveforms is then selected. This first group comprises a reference control element, preferably, an element at or near the end of the array, and a predetermined number of elements on either side, or to one side of the reference element.

A local optimum time compensation value is then calculated as above for the first group. A first global time compensation profile is then estimated by interpolation over the reference element and the elements at either end of the array. Note that, in this case, there will be two control points, namely, the reference element and the element at one end, the other end element remaining at the initial compensation value. A two-point waveform similarity factor—WSF2—is then evaluated for the first global time compensation profile.

Thereafter secondary control points are chosen between the first reference control point and either end of the array, for example, at or near ¼ and ¾ the width of the array. Element groups are then selected around or adjacent to each of these secondary control points and locally optimum time compensation values are calculated for each secondary group (control point) as described above. Yet another global time compensation profile is then formed by interpolation though the first local optimum value and the local optimum values for the secondary groups. A four-point WSF—

WSF4—is then calculated as before for this new global profile. If WSF4 differs from WSF2 by less than some experimentally or arbitrarily set threshold or percentage, then the system can assume that additional subdivision of elements and calculation of a global time delay profile with finer resolution would not yield a WSF better by more than the threshold than what the second profile provides, and can therefore accept the second global profile as the final one.

Otherwise, additional control points can be selected between each of the secondary and first points, so that, for example, eight control points (counting one end) would be spaced across the array at intervals of 1/8th the width. A new local optimization (for the new control points), global estimation and eight-point WSF8 determination can then be done for the whole array. As before, if WSF8 differs by less than the threshold amount or percentage from WSF4, then the system can take the corresponding global time compensation profile as the final one; otherwise, the array is further subdivided until WSF(i*2) differs from WSF(i) by less than the threshold amount or percentage.

Optimized Time Compensation for 2-D Array

Figure 3:
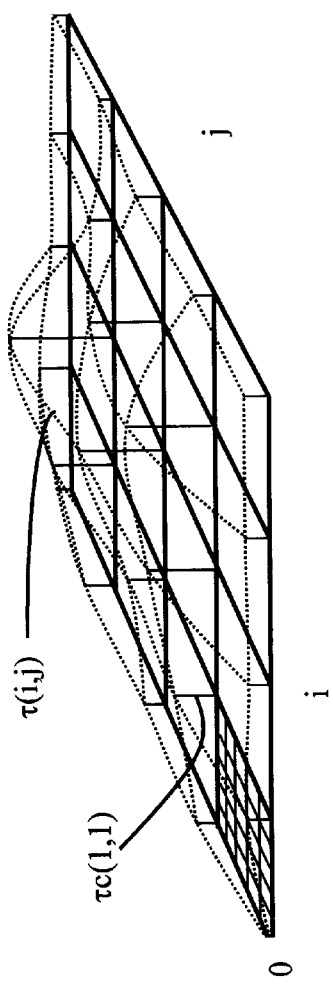
FIG. 3 illustrates an optimized time compensation profile for a 2-D array.

The invention is also able to determine a time compensation profile for waveforms generated by a two-dimensional array using the same methods as described above for the linear array: selection of control points and grouping of received waveforms; adjustment of each control point in turn and interpolation of the time delays of the other waveforms in the group; and, finally, after a locally determined optimum is calculated for each control point, global interpolation over all elements, and preferably through the time delays of all optimized control points to obtain a global time compensation profile. FIG. 3 illustrates this 2-D embodiment of the invention.

In FIG. 3, an M-by-N array of elements is shown as a grid (i,j) of elements, with corresponding waveforms. Merely by way of example, assume that the array is partitioned into 5-by-5 element groups and that the control element in each group is chosen to be the corner elements, which thus lie at the lines of intersection of adjacent groups. For the sake of simplicity, only the initial group, that is, the group lying closest to the arbitrarily selected origin 0, is shown divided into its 25 component elements/waveforms.

As before, the time delay for the control waveform is jittered; the time delays for the other waveforms in the group are determined using 2-D (surface) interpolation; WSF is calculated as before (only with two indices—i, j—instead of just i); and the time compensation $\tau c(i,j)$ (here: $\tau(1,1)$) for the control element is taken as the one that maximizes WSF. The optimum time compensation values of the other control points are then determined, preferably with interpolation including all previously optimized control points, and so on until an optimum time compensation is found for all control waveforms. An interpolating surface $\tau(i,j)$ is then calculated so as to pass through all (or, in some best-fit sense, optimally close to) the locally optimized time delay values, which are illustrated in FIG. 3 as line segments extending up from the respective control points.

The theory and implementation of interpolating or approximating surfaces are well known. In the preferred embodiment of the invention, spline surfaces are used to obtain $\tau(i,j)$, for the same reasons that spline curves (1-D) are preferred in the case of the linear array.

System Components

Figure 4:
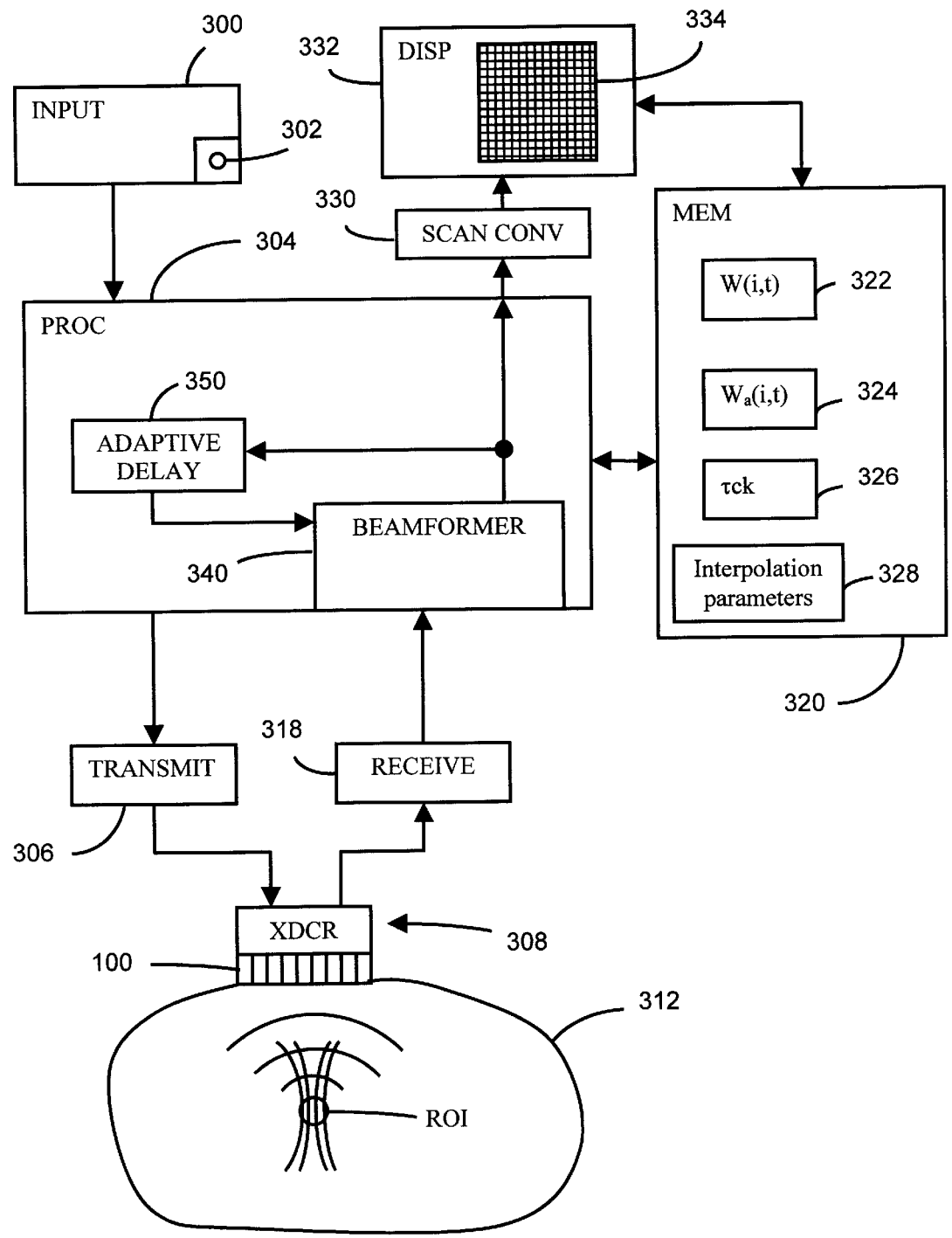
FIG. 4 shows the main components of the ultrasonic imaging system according to the invention.

FIG. 4 shows the main components of an ultrasonic imaging system suitable for use in implementing the invention. The user enters various conventional scan and control parameters into an input unit 300, which typically includes such devices as a keyboard 302, knobs and buttons. The input unit is connected to a processing system 304, which will typically be an electrically connected and cooperating group of processors such as microprocessors and digital signal processors, and will include all necessary system and application software. The processing system 304 may, however, also be implemented using a single processor as long as it is fast enough to handle the various tasks described below.

As in known systems, the processing system 304 sets, adjusts, and monitors the operating parameters of a conventional transmission and control circuit 306. This control circuit 306 forms the transmit waveform by generating and applying electrical control and driving signals to an ultrasound transducer 308, which includes the array 100 of individually controllable piezoelectric elements. As is well known in the art, the piezoelectric elements generate ultrasonic waves when the electrical signals of the proper frequency are applied to them.

The transducer 308 is placed against a portion 312 of the body of a patient, and by varying the phasing, amplitude and timing of the driving signals for the transducer array elements, ultrasonic waves are focused to form the transmit beam. The beam is focused on the interrogation region, that is, the region of interest ROI that is to be imaged.

The ultrasonic echoes from the beam transmitted into the interrogation region return to the array 100 in the transducer 308. As is well understood, the piezoelectric elements in the array convert the small mechanical vibrations caused by the echoes into corresponding electrical signals. This is also discussed above.

Amplification and other conventional signal conditioning is then applied to the echo signals by a reception controller 318. The reception controller 318, all or part of which is normally integrated into the processing system 304 itself, converts the ultrasonic echo signals (which are typically at radio frequencies, on the order of a few to tens of megahertz) into lower frequency ranges for processing, and may also include analog-to-digital conversion circuitry. This processing includes, as needed, such known signal conditioning as time-gating, gain compensation, and diffraction compensation, in order to identify the echo signals from the interrogation region. Part of the reception circuitry will, as is well known, include analog-to-digital conversion of the signals from the different array elements. The type of conventional signal processing needed will in general depend on the particular implementation of the invention and can be chosen using known design methods. This is well known in the art of diagnostic ultrasound.

Note that it is not necessary according to the invention that the transducer 308 be placed against the patient's body from without. Rather, the transducer may also be maneuvered inside the patient's body and the beam can be focused on the interrogation region from inside. This is the case with, for example, transesophageal probes. It would also be possible to implement the invention using separate transducer for transmission and reception, although this has obvious practical disadvantages.

A conventional memory 320 is also included in order to store, among other conventional data and code, a digital representation of the received waveforms W(i,t), the adjusted waveforms $W_a(i,t)$, the time compensation values τck and the interpolation parameters in respective memory portions 322, 324, 326, 328.

A display system 332 is preferably included in order to display for the user the image and visual feedbacks for user interface. The display system preferably includes a conventional monitor 334. The display system 322 also includes known circuitry for scan conversion and for driving the display, as needed. These circuits are well known and are therefore neither specifically illustrated nor described further.

Note that the display system may also include part or all of the input device 300, for example, in the case in which commands are input using displayed touch panels. Such techniques and how they are implemented are well-known in the field of graphical user interfaces.

The processing system 304 preferably also includes a beamformer 340, which may, however be implemented as a separate component that is connected to the processing system. Beamformers are well known in the art, and will include conventional software and hardware components that perform such functions as apodization.

One additional component of the processor, which is preferably implemented in software, is an adaptive delay module 350, which performs the various processing steps discussed above in conjunction with FIG. 1 and: Selection of control points and element groups, repeated calculation and evaluation of WSF, and local and global interpolation. The adaptive delay module is then functionally connected to the beamformer in order to apply the final, global time compensation profile to the receive waveforms. The optimized, beamformed output is then passed on to subsequent processing circuitry such as the scan converter 330.

Note that it will in general not be necessary to calculate an optimum time compensation profile for each received beam, since the orientation of the transducer and the geometry and properties of the interrogation region and ROI will seldom change significantly from one beam to next, due to the continuity of tissue structures. Instead, the same $\tau(i)$ can typically be used over many beams.

How long a calculated $\tau(i)$ is used may be either fixed, for example, for a predetermined number of receive beams, or selected by the user. For example, the user, looking at the displayed image, might suspect or even be able to see that an image is not as sharp as desired, or he may simply wish to make sure that a particular image has the best possible contrast. Using any conventional input device, for example, a touch panel on the a display, the user could then indicate to the processing system that it should determine a new time compensation profile.

User Interface for Adaptive Time Compensation

Figure 5:
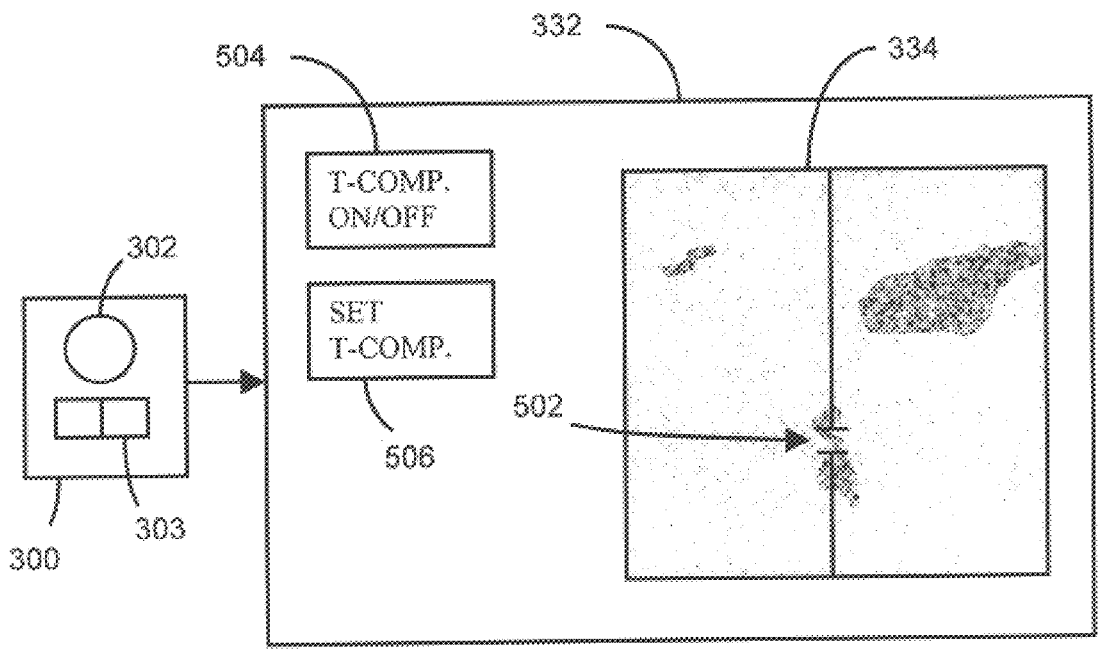
FIGS. 5 and 6 illustrate a graphical user interface, in two respective states, that allows a user to control certain aspects of the time compensation made possible by this invention.
Figure 6:
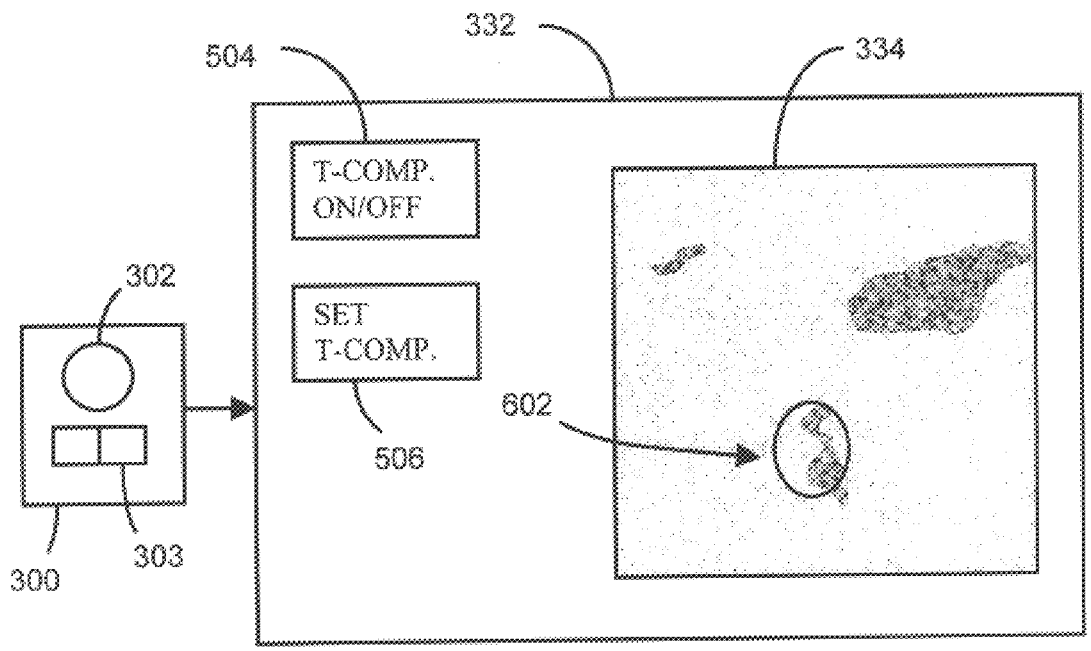

FIGS. 5 and 6 illustrate a graphical user interface that allows a user not only to turn time compensation on and off altogether, but also to select for which ROI the system should determine an optimal time compensation profile.

In these figures, the input device 300 is shown as including both a cursor control device 302 (here: a trackball) and buttons 303. This is of course functionally equivalent to a standard mouse, which may also be used. Two touch panels 504, 506 are shown as being displayed (using known techniques), labeled "T-Comp On/Off" and "Set T-Comp.," respectively, where T-Comp abbreviates "time compensation." Of course, other text, or icons, may be used. Using these touch panels (or by clicking on equivalent icons, entering predetermined keystrokes, etc.) the user, by touching them, turns time compensation on and off (that is, whether a calculated time compensation profile should be applied to receive, and preferably also to subsequent transmit, beams), and directs the processing system to recalculate the optimum time compensation profile as above, given the waveforms forming the basis of the currently viewed image.

Within the displayed image in FIG. 5 is also a displayed a range gate symbol 502, which serves as a cursor and indicates the vector and depth interval for choosing a time compensation base point, which also defines the ROI within the image. Note that the processing system is able to determine which portion of the physical interrogation region corresponds to the point in the displayed image pointed to by the cursor, since each point in the displayed image corresponds to a known point in the interrogation region.

Assume now that the user is particularly interested in the structure (shown slightly darker in the image) located near the bottom center of the displayed image. He then maneuvers the cursor (using, for example, the trackball) to point to this structure and touches the "Set T-Comp." touch panel 506. Sensing this, the processing system then sets as the ROI the portion of the interrogation region corresponding to the cursor position (the time compensation base point), and sets the transmit control circuit 106, using known methods, to focus the ultrasound beam on the selected ROI. The processing system then also causes to be displayed on the screen a compensation region marker, such as the ellipse 602, whose boundary corresponds to the region within which the system will apply the calculated time compensation profile. The compensation region marker thus corresponds to a time compensation region. The system thereafter calculates a time compensation profile for this ROI as described above. In this case, the user-selected time compensation region forms the ROI and thus the basis for calculation of the optimum time compensation profile. This profile is then applied at least to the compensation region, and preferably (since more than one time compensation profile would be and computationally demanding) to the entire displayed region.

This of course means that the time delay profile will not be "optimum" in any sense for the image as a whole, since it is calculated based solely on the receive beams received from the selected time compensation region. On the other hand, the larger a region any given time delay profile is based on, the worse it will generally be for any particular portion of the larger region. The assumption here is, however, that the user is particularly interested in being able to clearly distinguish and view structures in the smaller ROI, such that worsened contrast in other regions of the display is not a concern.

As long as the cursor is not moved, the system preferably removes the range gate symbol 502 from the display in order to obstruct as little of the image as possible. The compensation region marker 602 is, however, preferably still displayed until either the user turns off time compensation (using the touch panel 504), or the user selects a new ROI as the basis for time compensation. The cursor is preferably redisplayed when the user moves it.

The size, orientation and shape of the compensation region marker 602, and the corresponding region of compensation, may be determined in different ways. One way is simply to have a region of compensation with the axes of the ellipse (or parameters of some other shape) defined as a certain distance from the userselected ROI. It may also be a predetermined function of the size of the range gate. In general, it may be determined based on experimental data that indicates the size of a region for which the image resolution is typically improved by the time-delay adjustments derived in this invention.

One advantage of this interface is that time compensation is determined and applied only to a sub-set of the displayed image. This will in general improve the contrast and quality of the displayed ROI, although typically at the cost of poorer image quality for other portions of the display, since they will be using a time compensation optimized for a completely different region that is often so far away that the image information is substantially uncorrelated. The system preferably includes a conventional "zoom" feature to allow the user to zoom in on the region within the marker 602.

Another advantage of this interface if that, on a stationary object, the user can repeatedly press the "Set T-Comp." touch panel (or button) to iteratively improve the time compensation profile: The improved time compensation profile provided by the invention leads to improved transmit focus, which in turn improves the accuracy of the calculation of the time compensation profile, and so on. This iterative improvement terminates when the user moves the cursor, or if the "Set T-Comp." panel is pressed and when time compensation is turned off.

This iterative procedure can be summarized as follows: a) viewing the displayed image, the user moves the range gate symbol to a portion of greatest interest of the image; b) the user the presses a button or touch-screen icon, or key, etc., to initiate correction; c) the system then moves the transmit focal point to the depth of the selected region of interest; and d) the system then iteratively corrects both the transmit and receive beamforming based on the time compensation profile, as explained above, until some predetermined criterion of acceptability is met. This criterion may be as simple as that the user has moved the cursor or de-selected this iterative time compensation correction, for example by releasing the button, once again touching the icon, etc. Another criterion might be automatic; for example, if a subsequent calculated time compensation profile differs by less than some amount, according to any predetermined metric, from the one previously calculated.

Yet another advantage of this interface is that it avoids the display flickering that would otherwise be caused if the time compensation profile were updated continuously, that is, for every receive beam. Yet another advantage of this interface is that, by eliminating the need for continuous time-delay estimation for all beams, the data transfer and processing requirements of the system are much reduced and can be met with common general-purpose processors. This in turn enables a flexible and economic implementation of phase aberration correction.

I claim:

1. An ultrasound imaging method comprising the following steps:
   transmitting into a region of interest of a patient's body a transmit beam of ultrasound from a plurality of elements in a transducer array;
   receiving an echo signal back from the region of interest, each transducer array element thereby generating a respective receive waveform, the waveforms together constituting a receive beam;
   for at least one group of at least three receive waveforms, maximizing a group waveform similarity factor, which is a predetermined function of the waveforms in the group;
   for each group of waveforms, determining a locally optimal time compensation value;
   calculating a global time compensation profile as a predetermined function of the locally optimal time compensation values;
   time-shifting each receive waveform according to the global time compensation profile, thereby forming a time-compensated receive beam; and
   generating at least one image of the region of interest as a predetermined function of the time-compensated receive beam.

2. A method as in claim 1, further including the following steps:
   a) for each group, selecting a control point and corresponding control waveform, both of which correspond to a control element of the array;
   b) for a first one of the groups, selecting an initial compensation time for the waveforms in the first group;
   c) time-shifting the control waveform by a local time shift amount;
   d) determining a local time compensation profile by interpolation of time delays at the control points;
   e) calculating a local waveform similarity factor as a predetermined function of the local time compensation profile;
   f) repeating steps c)-e) and thereby obtaining a plurality of values of the local waveform similarity factor;
   g) setting as the locally optimal time compensation value for the first group the local time shift amount for which the corresponding local waveform similarity factor is a maximum;
   h) for each waveform group other than the first:
      setting as the initial compensation time the locally optimal time compensation value of the preceding waveform group; and
      repeating steps c)-e) for the respective waveform group, thereby determining the locally optimal time compensation values for all the groups.

3. A method as in claim 2, in which the global time compensation profile is calculated by interpolating from the initial time compensation value of the first group and over the locally optimal time compensation values for all the groups.

4. A method as in claim 2, in which the waveform similarity factor is a predetermined function of the sum of the waveforms in each respective group time-shifted according to the respective local time compensation profile.

5. A method as in claim 4, in which the waveform similarity factor is proportional to the r.m.s. value of the sum of the waveforms in each respective group.

6. A method as in claim 1, in which:
   the array comprises a two-dimensional array of elements;
   each group corresponds to a two-dimensional portion of the array; and
   the local time compensation profile for each group is determined by interpolation using interpolating surfaces.

7. A method as in claim 1, further including the step of correcting the transmit beam according to the global time compensation profile.

8. A method as in claim 7, further including the following steps:
   a) selecting a portion of greatest interest of the generated image;
   b) moving a transmit focal point to the depth of the portion of greatest interest;
   c) calculating the global time compensation profile based on received waveforms only from the portion of greatest interest;
   d) correcting transmit and receive beamforming based on the global time compensation profile; and
   e) performing steps c) and d) until a predetermined criterion of acceptability is met.

9. An ultrasound imaging method comprising the following steps:
   a) transmitting into a region of interest of a patient's body a transmit beam of ultrasound from a plurality of elements in a transducer array;
   b) receiving an echo signal back from the region of interest, each transducer array element thereby generating a respective receive waveform, the waveforms together constituting a receive beam;
   c) grouping the array elements into a predetermined number of groups;
   d) for each group, selecting a control waveform corresponding to a control element of the array;
   e) for a first one of the groups, selecting an initial compensation time for the waveforms in the first group;
   f) time-shifting the control waveform by a local time shift amount;
   g) determining a local time compensation profile by interpolation between the local time shift amount and the initial compensation time;
   h) calculating a local waveform similarity factor as the r.m.s. value of the sum of the waveforms in the group time-shifted according to the local time compensation profile;
   i) repeating steps f)-h) and thereby obtaining a plurality of values of the local waveform similarity factor;
   j) setting as a locally optimal time compensation value for the first group the local time shift amount for which the corresponding local waveform similarity factor is a maximum;
   k) for each waveform group other than the first:
      setting as the initial compensation time the locally optimal time compensation value of the preceding waveform group; and
      repeating steps f)-h) for the respective waveform group, thereby determining the locally optimal time compensation values for all the groups;
   l) calculating a global time compensation profile by interpolating from the initial time compensation value of the first group and over the locally optimal time compensation values for all the groups;
   m) time-shifting each receive waveform according to the global time compensation profile, thereby forming a time-compensated receive beam; and
   n) generating an image of the region of interest as a predetermined function of the time-compensated receive beam.

10. An ultrasound imaging system comprising:
   an ultrasound array including a plurality of array elements;
   transmit circuitry activating the array elements to transmit into a region of interest of a patients body a transmit beam of ultrasound;
   reception circuitry converting echo signals received by the array elements into respective receive waveforms, the waveforms together constituting a receive beam;
   processing means including adaptive delay means connected to a beamformer, the adaptive delay means being provided:
      for at least one group of at least three receive waveforms, for maximizing a group waveform similarity factor, which is a predetermined function of the waveforms in the group;
      for each group of waveforms, for determining a locally optimal time compensation value;
      for calculating a global time compensation profile as a predetermined function of the locally optimal time compensation values;
   for time-shifting each receive waveform according to the global time compensation profile, thereby forming a time-compensated receive beam; and
   for generating an image of the region of interest on a display as a predetermined function of the time-compensated receive beam.

11. A system as in claim 10, the adaptive delay means being further provided:
   a) for each group, for selecting a control waveform corresponding to a control element of the array;
   b) for a first one of the groups, for selecting an initial compensation time for the waveforms in the first group;
   c) for time-shifting the control waveform by a local time shift amount;
   d) for determining a local time compensation profile by interpolation between the local time shift amount and the initial compensation time;
   e) for calculating a local waveform similarity factor as a predetermined function of the local time compensation profile;
   f) for repeating steps c)-e) and thereby obtaining a plurality of values of the local waveform similarity factor;
   g) for setting as the locally optimal time compensation value for the first group the local time shift amount for which the corresponding local waveform similarity factor is a maximum;
   h) for each waveform group other than the first:
      for setting as the initial compensation time the locally optimal time compensation value of the preceding waveform group; and
      for repeating steps c)-e) for the respective waveform group, thereby determining the locally optimal time compensation values for all the groups.

12. A system as in claim 10, in which the array comprises a two-dimensional array of elements; and each group corresponds to a two-dimensional portion of the array.

13. An ultrasound imaging system comprising:
   an ultrasound array including a plurality of array elements;
   transmit circuitry activating the array elements to transmit into a region of interest of a patient's body a plurality of transmit beams of ultrasound;
   reception and beamforming circuitry converting, for each transmit beam, echo signals received by the array elements into a corresponding receive beam;
   scan conversion means for converting each receive beam into a predetermined display format;
   display means for displaying the receive beams as a visual, displayed image of the region of interest;
   input means controlled by the user for selection and designation of a portion of the displayed image as a compensation region;
   time delay compensation means for calculating an optimum time compensation profile as a predetermined function of those portions of those receive beams that correspond to the displayed compensation region and for applying the optimum time compensation profile to the portion of the receive beam corresponding to at least the displayed compensation region.

14. An ultrasound imaging system as in claim 13, in which the transmit circuitry is provided for focusing the transmit beams onto a time compensation base point, which is selected by the user using the input means, the compensation region being a portion of the displayed image that includes the time compensation base point.

15. An ultrasound imaging system as in claim 14, in which the transmit circuitry and reception and beamforming circuitry together form means for calculating the global time compensation profile based on received waveforms from the compensation region and correcting transmit and receive beamforming based on the global time compensation profile until a predetermined criterion of acceptability is met.

* * * * *